United States Patent [19]
Pettersson et al.

[11] Patent Number: 6,065,597
[45] Date of Patent: *May 23, 2000

[54] CATHETER PACKAGE

[75] Inventors: Agneta Pettersson, Göteborg; Jan Utas, Kungsbacka, both of Sweden

[73] Assignee: Astra Aktiebolag, Sodertalje, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/875,345

[22] PCT Filed: Jun. 12, 1997

[86] PCT No.: PCT/SE97/01033

§ 371 Date: Jul. 29, 1997

§ 102(e) Date: Jul. 29, 1997

[87] PCT Pub. No.: WO97/47349

PCT Pub. Date: Dec. 18, 1997

[30] Foreign Application Priority Data

Jun. 14, 1996 [SE] Sweden ................................. 9602352

[51] Int. Cl.[7] ..................................................... B65D 83/10
[52] U.S. Cl. ........................................... 206/364; 206/439
[58] Field of Search .................................. 206/364, 439, 206/210, 213.1

[56] References Cited

FOREIGN PATENT DOCUMENTS 0629415 12/1994 European Pat. Off. .
0677299 10/1995 European Pat. Off. .
2131384 6/1984 United Kingdom .

*Primary Examiner*—David T. Fidei
*Attorney, Agent, or Firm*—White & Case LLP

[57] ABSTRACT

A catheter package (10; 110; 210) comprising a catheter (1; 101; 201) positioned within an inner container (2; 102; 202) permeable to a sterilizing agent, for example an ethylene oxide gas. An outer container (3; 103; 203) which prevents access of moisture to the interior thereof encloses the inner container and catheter assembly. Two or more catheters may be stored in individual inner containers within the outer container.

13 Claims, 3 Drawing Sheets

CATHETER PACKAGE

TECHNICAL FIELD OF THE INVENTION

The present invention relates to a catheter package, and to a method of packaging catheters in the same.

BACKGROUND TO THE INVENTION

Catheters having exterior coatings have been known for many years. Typically the coating is a hydrophilic layer designed to reduce the coefficient of friction in the wet condition, so that the catheter may be inserted relatively painlessly into the urethra of the patient, and likewise removed therefrom when required.

Typical examples of such catheters are made known in European patent specifications EP-B-0093093 (Astra Meditec AB) and EP-B-0217771 (Astra Meditec AB). EP-B-0093093 discloses a process for providing a polymer surface, such as a urinary latex catheter, with a primary coating including an isocyanate compound, and a secondary coating including polyvinylpyrrolidone. EP-B-0217771 discloses a method of forming an improved hydrophilic coating in order to retain the slipperiness for a longer time on a substrate, such as a urinary PVC catheter, by applying a solution comprising a solvent having an osmolality-increasing compound such as sodium chloride.

Catheters are conventionally packaged in a paper package, in order to allow them to be sterilized before they are used. Such sterilization typically is performed at the time of manufacture, using techniques well-known in the art such as gamma-irradiation or fumigation with ethylene oxide gas. If ethylene oxide is used, it must be allowed to have access to the catheter surface, and a paper package allows this to occur. The conventional approach is to use a paper which is permeable to ethylene oxide, grid-lacquered with polyethylene and welded around its edge to a laminate of, for example, polyethylene-polypropylene or polyethylene-polyethylene terephthalate, or possibly polyethylene-nylon.

Applicant has observed that a problem encountered with coated catheters is that the surface of the catheter can become sticky and adhere to the paper of the package causing the coating on the catheter to be damaged, destroyed or mutilated.

Inserting a plastics material adjacent to the interior surface of the paper has been suggested, creating a loose paper-plastic laminate sealed just around its edges so that the catheter does not come into immediate contact with the paper. However, this has the disadvantage that a barrier is now in place which prevents penetration of ethylene oxide into the interior of the package so as to be brought into contact with the surface of the catheter. Such a package could only effectively be sterilized by irradiation, although an alternative is to provide a number of slits in the plastics material, thin enough to prevent the catheter surface from coming into direct contact with the paper and yet capable of opening wide enough to allow access of ethylene oxide at the required time.

This clearly means that the manufacturing process is made more complicated than would be desirable. In particular, the slits in the plastics material have to be carefully regulated so that they do not permit contact of the catheter surface with the paper, without in any way hindering sterilization with ethylene oxide.

DISCLOSURE OF THE INVENTION

There is therefore a need for an improved catheter package and according to the present invention there is provided a catheter package comprising a surface coated catheter, for example a hydrophilic outer surface coated catheter, and a container which encloses the catheter and permits the passage of a sterilizing agent for the catheter therethrough, for example an ethylene oxide gas, characterised in that the container is an inner container and that the catheter package further comprises an outer container which encloses the inner container and prevents or substantially prevents access of moisture to the interior thereof.

Such a package can overcome the disadvantages inherent in the prior art whilst still being simple to manufacture. It thus appears that the sticky surface of the catheter is caused by the gradual ingress of moisture into the package during storage.

The outer container of the package may be formed from a single layer of a plastics material such as polyethylene or poly(vinylidene dichloride) (PVDC). However, a better moisture-tight barrier may be achieved by using a laminate including a metallic layer such as aluminium. Typically a laminate of aluminium and polyethylene could be used, with the polyethylene on the interior of the outer container. Such a material would be quite fragile, but this may be compensated for by providing a strengthening outer layer of a plastics material such as polyester or oriented polypropylene, for example biaxially oriented polypropylene.

Applicant has also found that a moisture-tight barrier can be obtained by using a silicon oxide, for example silicon dioxide, in the construction of the outer container. The silicon oxide can be supported in a matrix material such as a polyester, polyethylene terephthalate (PET), nylon or polypropylene or as supplied by Mitsubishi under the trade name Techbarrier-S and may further be used as one layer of a laminate used to construct the outer container. If need be, a strengthening outer layer of a plastics material can again be used in the outer container construction.

Alternatively, a metallised film such as a metallised film of PET with aluminium oxide may be used. The metal content of this is very small, which is environmentally better, and yet Applicant has found it to be a good moisture barrier. Nylon and polypropylene are alternatives to polyethylene terephthalate in such films.

Poly chloro tri fluoro ethylene (PCTFE) may also be mentioned as a possible barrier material for the outer container construction.

One catheter may be stored in each package. However, as catheters are generally used once or a very few times and then replaced, two or more catheters may be stored in individual inner containers within a single outer container.

In such a case, it would be an advantage if the outer container could be sealed again whenever an inner container containing a catheter is taken out. This may be achieved by providing a means for re-closing the outer container, such as a zip fastener or a resealing tape.

Even so, it is possible that small amounts of moisture may diffuse through the outer container into the cavity between the inner and outer containers during prolonged storage, or enter when a catheter is removed if a re-closing means is provided. Applicant has found that diffusion of moisture can occur particularly when the outer container comprises a single polymeric layer such as polyethylene. This problem may be obviated by placing a desiccant in this cavity. A typical desiccant would comprise a sachet of silica gel, or a molecular sieve or calcium chloride.

Applicant has found that sometimes the use of plasticiser, or solvents in glue, during the manufacture of the catheter or the outer container can cause malodorous fumes to develop in the cavity between the inner and outer containers during prolonged storage. This may be obviated by placing a deodorant material in this cavity. A typical deodorant material would comprise a sachet of active carbon.

The package is particularly, although not exclusively, suitable for use in combination with a catheter having a hydrophilic coating. Such a coating is always more or less sensitive to water. Examples of moisture-sensitive coatings are polyethylene oxide, poly(vinylpyrrolidone) (PVP) and cellulose polymers such as hydroxyethylcellulose or hydroxypropylcellulose. The coating may include an osmolality-increasing compound such as sugar, urea or an inorganic salt. Typically such compounds are crystalline in form and readily soluble in water. Suitable inorganic salts include sodium and potassium chlorides, iodides, nitrates, citrates and benzoates.

According to the invention there is further provided a method of manufacturing a catheter package comprising the steps of enclosing a surface coated catheter in an inner container which permits access of a sterilizing agent therethrough to the enclosed catheter and exposing the inner container and catheter assembly to the sterilizing agent sufficiently to sterilize the catheter characterised by the provision of the further step of enclosing the inner container and catheter assembly in an outer container which prevents or substantially prevents access of moisture to the interior thereof.

BRIEF DESCRIPTION OF THE DRAWINGS

Embodiments of the invention will now be described, by way of example, with reference to the attached drawings in which.

DETAILED DESCRIPTION OF EMBODIMENTS OF THE INVENTION

Figure 1:
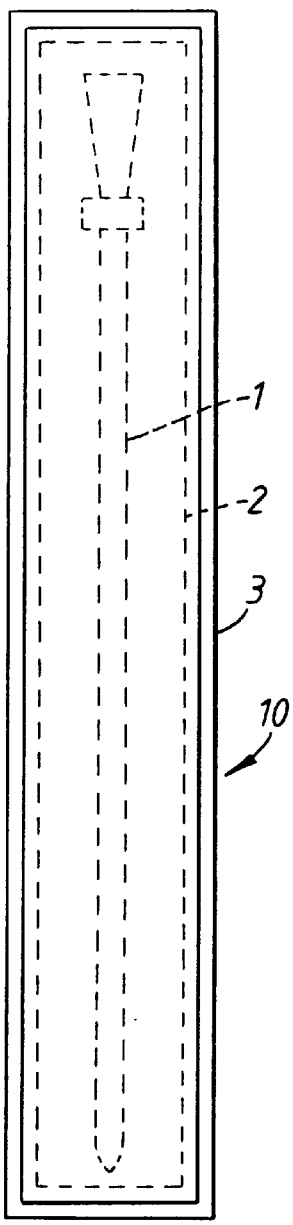
FIG. 1 is a view of a catheter package according to a first embodiment of the present invention comprising an inner container which encloses a catheter and an outer container which encloses the inner container.

Referring to FIG. 1 and FIGS. 2A to 2C, a catheter package 10 according to a first embodiment of the present invention comprises a catheter 1 positioned within an interior pouch 2 which is itself positioned within an exterior pouch 3. The catheter 1 may, for example, be a urinary PVC catheter with a hydrophilic coating which includes an osmolality-increasing compound such as sodium chloride, as disclosed in EP-B-0217771.

The construction of the interior pouch 2 is such that it is permeable to ethylene oxide gas. As can be seen from FIG. 2B, the interior pouch 2 is formed from a first boundary wall section comprising a layer of paper 10 grid-lacquered with a layer of polyethylene 9 and a second boundary wall section comprising a laminate of, for example, a layer of polyethylene 8 and a layer of polypropylene 7 welded to the edge of the first boundary wall section. A laminate of polyethylene-polyethylene terephthalate, or possibly polyethylene-nylon, could also be used for the second boundary wall section, and the edges could also be sealed by crimping or folding. Instead of paper, Tyvek™, a non-woven material of polyethylene fibres supplied by DuPont, might be used in the first boundary wall section. In this case, the additional layer of polyethylene 9 would be unnecessary as the non-woven material would itself be able to form a good seal by welding.

Figure 2A:
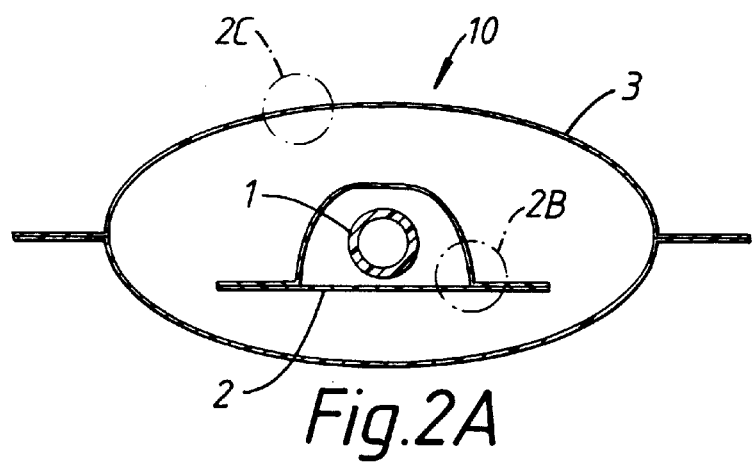
FIG. 2A is a cross-sectional view of the catheter package of FIG. 1.
Figure 2B:
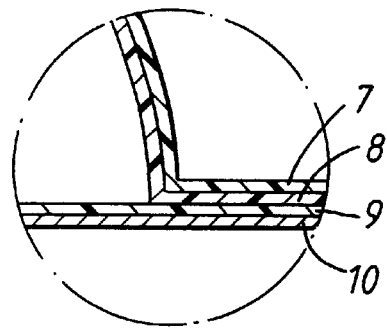
FIG. 2B is a cross-sectional view of the construction of the boundary wall of the inner container of FIG. 1.
Figure 2C:
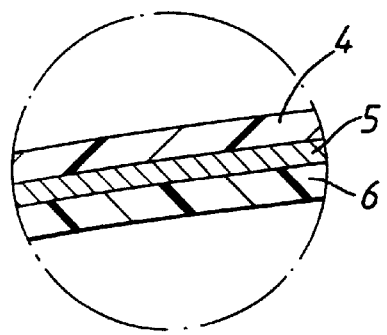
FIG. 2C is a cross-sectional view of the construction of the boundary wall of the outer container of the catheter package of FIG. 1.

The construction of the exterior pouch 3, on the other hand, is such that it prevents the access of moisture to the interior pouch 2. As shown in FIG. 2C, the exterior pouch 3 is formed from a laminate composed of a layer of aluminium 5 and a layer of polyethylene 6, with the polyethylene layer 6 being on the interior of the exterior pouch 3. An exterior layer of polyester 4 is supported on the aluminium layer 5. The edges of the exterior pouch 3 are sealed together by welding. Typical dimensions are 30 to 50 μm for the polyethylene layer 6, 8 to 10 μm for the aluminium layer 5 and 10 to 20 μm for the polyester layer 4.

Alternately, a layer comprising a silicon oxide may be substituted for the aluminium layer 5, for instance a layer of the silicon oxide barrier material sold by Mitsubishi under the trade name Techbarrier-S. An aluminium oxide could also be used to form the barrier layer as could PCTFE.

The catheter package 10 is assembled by firstly enclosing the catheter 1 in the interior pouch 2 and then exposing the interior pouch 2 to ethylene oxide gas until the catheter 1 becomes sterilized. The interior pouch 2 is then enclosed in the exterior pouch 3.

It has been found that the catheter package 10 gives a shelf-life of at least one year without the surface of the catheter 1 becoming sticky. The problem of damage occurring to the coating of the catheter 1 by adherence thereof to the paper layer 10 of the interior pouch 2 is therefore alleviated.

Figure 3:
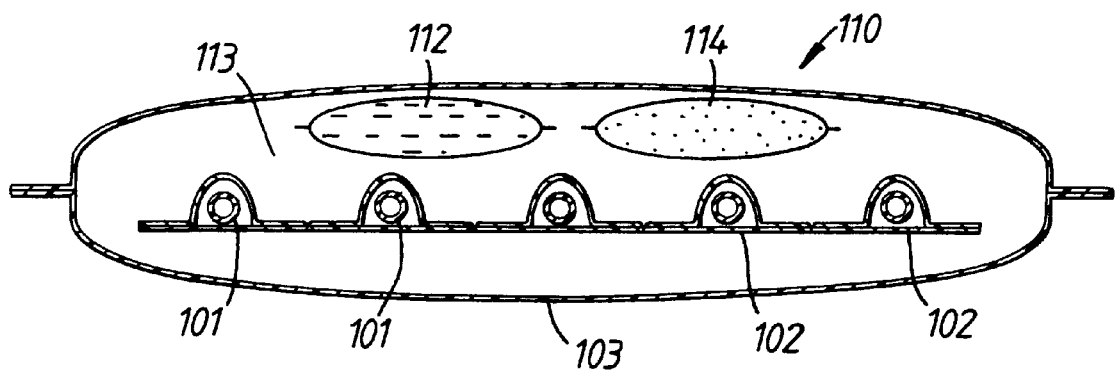
FIG. 3 is a cross-sectional view of a catheter package according to a second embodiment of the invention comprising a plurality of catheters within individual inner containers all enclosed within an outer container.
Figure 4:
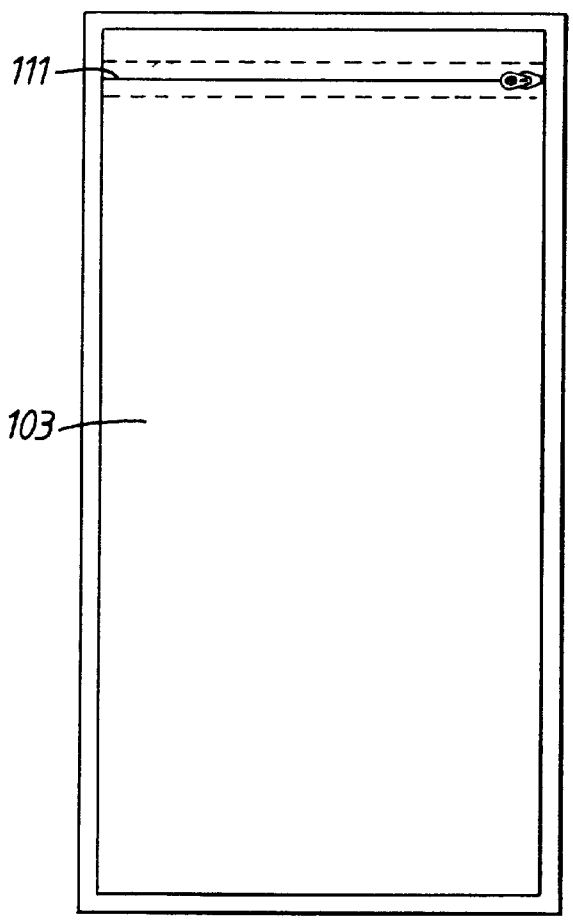
FIG. 4 is a further view of the catheter package shown in FIG. 3.

In FIGS. 3 and 4 there is shown a catheter package 110 according to a second embodiment of the present invention. In this instance a plurality of catheters 101 are stored in individual interior pouches 102 within a single exterior pouch 103. The constructions of the interior and exterior pouches 102, 103 are as in the first embodiment hereinabove described with reference to FIGS. 1 and 2A to 2C. However, in this case a zip-fastener 111 is made integral with the exterior pouch 103 for opening and closing the exterior pouch 103 to enable one interior pouch 102 at a time to be removed whilst minimising contact of the remaining interior pouches 102 with ambient air.

A desiccant comprising a sachet of silica gel 112 is also included in the cavity 113 between the exterior pouch 103 and the interior pouches 102. A deodorant material comprising a sachet of active carbon 114 is also provided in the same cavity 113.

The catheter package 110 also gives a shelf-life of at least one year without the surface of the catheters 101 becoming sticky. Furthermore, the user is not confronted by noxious fumes on opening the exterior pouch 103.

The catheter package 110 is manufactured by forming each interior pouch 102 about the catheter 101 that it contains and sealing the edges of the interior pouches 102 by welding them together. Ideally a number of interior pouches 102 may be manufactured as a single unit, joined at the edges so that they may be separated when required. The interior pouches 102 are then sterilized by exposure thereof to ethylene oxide gas and aerated to remove excess ethylene oxide. An optional irradiation step may be included.

The interior pouches 102 are collected together along with the sachets of silica gel 112 and active carbon 114. The exterior pouch 103 is then formed about these. The most expedient way of achieving this is to use a prefabricated pouch 103 in which three of the four edges have already been sealed together by welding. The contents are then inserted and the fourth edge of the exterior pouch 103 sealed together as well, again by welding.

Figure 5:
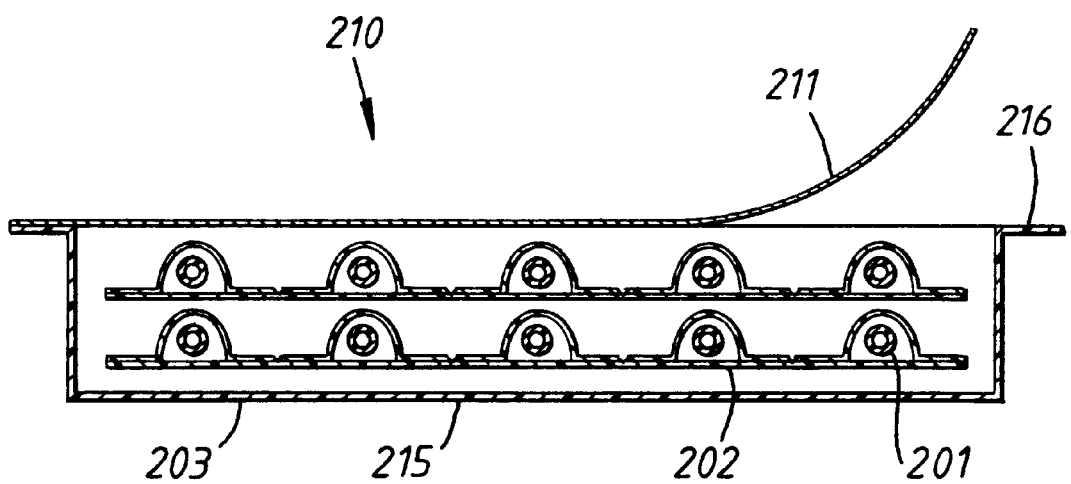
FIG. 5 is a cross-sectional view of a catheter package according to a third embodiment of the invention comprising a plurality of catheters within individual inner containers all enclosed within an outer container.

Turning now to FIG. 5, a catheter package 210 according to a third embodiment of the present invention comprises several catheters 201 stored in individual interior pouches 202 of the same construction as in the first embodiment hereinabove described with reference to FIGS. 1 and 2A to 2C which are in turn stored within a single exterior pouch 203. The exterior pouch 203 comprises a vacuum-formed tray 215 with a flat lid 216. The tray 215 and lid 216 are both made of a barrier material that prevents the access of moisture to the interior pouches 202 and may be formed from the same or different materials. Use of the same material is convenient though. As suitable materials there may be mentioned polypropylene, poly(vinylidene dichloride) (PVDC), a metallised film, and an aluminium laminate with polyethylene, polyester, polystyrene, polypropylene or nylon. The necessity to vacuum-form the tray 215 means that certain restrictions are imposed on its thickness, though any reasonable thickness of material may be used for the lid 216. A typical thickness for the tray 215 would be in the range of 400 to 600 $\mu$m, although if a stiffer material were used a thickness down to 100 or 200 $\mu$m is possible. The tray 215 could also be made of a foamed material, such as expanded polystyrene.

A means for opening and closing the exterior pouch 203 comprising a resealing tape 211 is made integral with the lid 216 of the pouch 203. Thus contact of the interior pouches 202 with ambient air is minimised.

The catheter package 210 is manufactured by collecting together the interior pouches 202 after exposing them to a sterilizing agent such as ethylene oxide gas and forming the exterior pouch 203 about these. The most expedient way of achieving this is to place the interior pouches 202 within the well of the vacuum-formed tray 215 of the exterior pouch 203 and then sealing the edges of the lid 216 of the exterior pouch 203 onto the tray 215 by welding. The depth of the tray 215 can, as shown, be selected so as allow more than one layer of catheters 201 to be inserted.

What is claimed is:

1. A catheter package comprising a hydrophilic surface coated catheter, an inner container and an outer container, wherein the inner container encloses the catheter and permits the passage of a sterilizing agent through the inner container for sterilizing the catheter and the outer container encloses the inner container and substantially prevents access of moisture to the interior of the outer container.

2. The package as claimed in claim 1, wherein the outer container comprises a laminate comprising a metallic layer.

3. The package as claimed in claim 1, wherein the outer container comprises a layer comprising a silicon oxide.

4. The package as claimed in claim 2 or 3, wherein the outer container comprises a strengthening outer layer comprising a plastic material.

5. The package as claimed in claim 1, wherein the catheter and inner container form a catheter sub-assembly and the catheter package comprises one or more catheter package sub-assemblies within the outer container.

6. The package as claimed in claim 5 further comprising a means for repeated opening and closing of the outer container.

7. The package as claimed in claim 1 or 5, wherein a desiccant is disposed in between the inner and outer containers.

8. The package as claimed in claim 1 or 5, wherein a deodorant is disposed in between the inner and outer containers.

9. The package as claimed in claim 1, wherein the sterilizing agent is an ethylene oxide gas.

10. The package as claimed in claim 1, wherein the hydrophilic coating comprises an osmolaity-increasing compound.

11. The package as claimed in claim 1, wherein the hydrophilic coating comprises an inorganic salt selected from the group consisting of sodium and potassium chloride, iodides, nitrates, citrates and benzoates.

12. A method of manufacturing a catheter package comprising the following steps:

(a) enclosing a hydrophilic surface coated catheter in an inner container which permits passage of a sterilising agent through the inner container to the enclosed catheter;

(b) exposing the inner container and catheter assembly to the sterilising agent sufficiently to sterilise the catheter; and (c) enclosing the inner container and catheter in an outer container which substantially prevents access of moisture to the interior of the outer container.

13. The method as claimed in claim 12, wherein the sterilizing agent is an ethylene oxide gas.

* * * * *